United States Patent [19]

Burnett

[11] 4,045,873
[45] Sept. 6, 1977

[54] DENTAL ARTICULATOR

[76] Inventor: Walter L. Burnett, 4336 Covington Highway, Decatur, Ga. 30035

[21] Appl. No.: 700,141

[22] Filed: June 28, 1976

[51] Int. Cl.² .......................................... A61C 11/00
[52] U.S. Cl. ...................................................... 32/32
[58] Field of Search ........................................... 32/32

[56] References Cited

U.S. PATENT DOCUMENTS

| 1,050,933 | 1/1913 | Evans | 32/32 |
| 1,055,894 | 3/1913 | Evans | 32/32 |
| 1,687,864 | 10/1928 | Hill | 32/32 |
| 3,324,554 | 6/1967 | Dietrich | 32/32 |

*Primary Examiner*—Robert Peshock
*Attorney, Agent, or Firm*—Patrick F. Henry

[57] ABSTRACT

The present dental articulator provides a means for correcting most incorrect bites after the models have been mounted and permits the model to be removed and placed on another similar articulator in the same position. An articulator frame comprises a base having opposed side frame members but supports a pivoting frame attached thereto by pivot pin and coil spring arrangement. A bottom bracket removably mounted on the base supports a U-shaped model bar for the lower model with adjustment means thereon removably supporting the model frame. An upper bracket on the pivoting frame removably supports a U-shaped upper model bar for adjustment thereon. The upper and lower models are mounted and adjusted in fixed position and then may be removed and sent without the articulator to be remounted later in a similar articulator.

19 Claims, 7 Drawing Figures

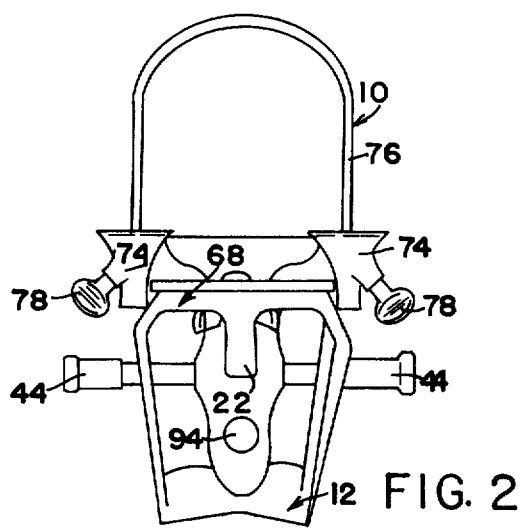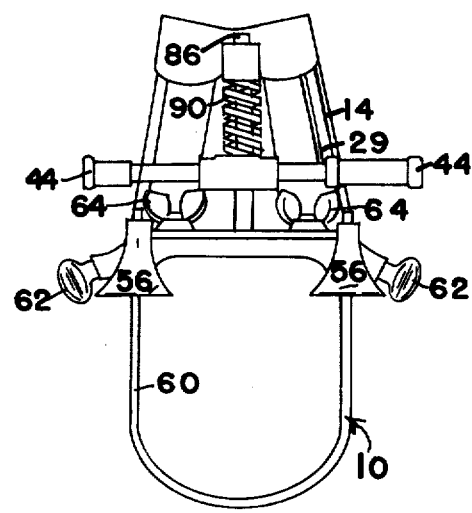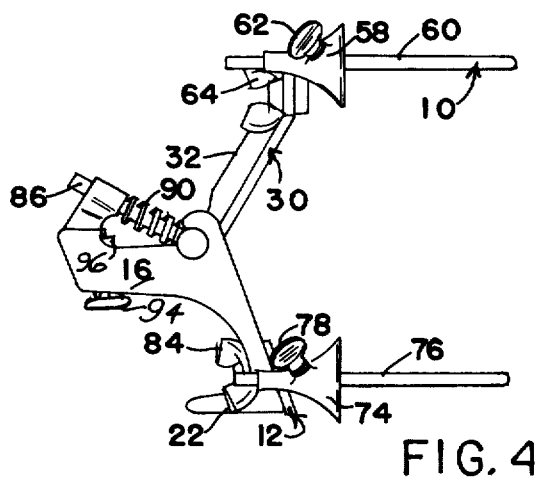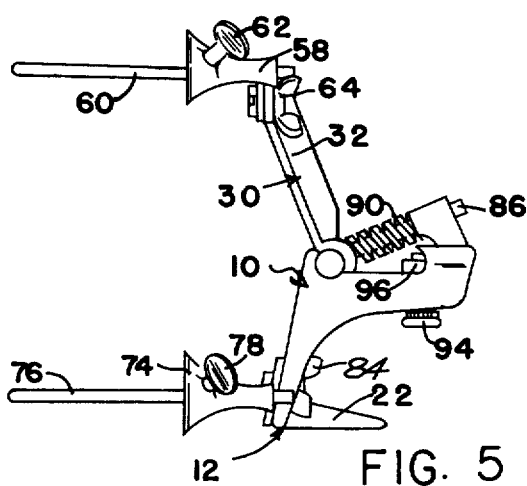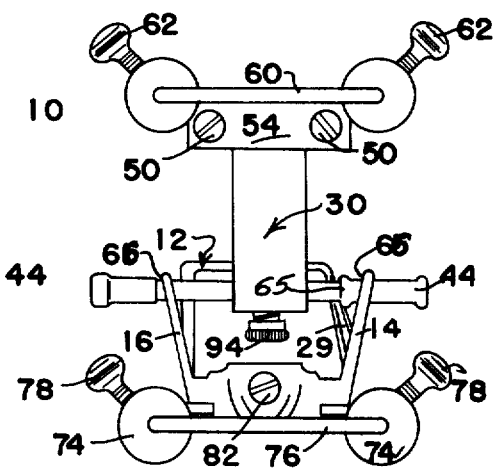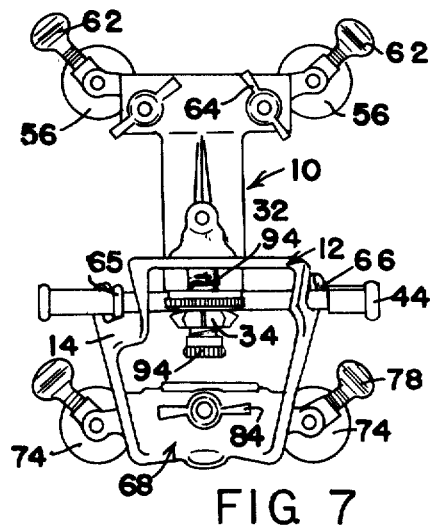

DENTAL ARTICULATOR

BACKGROUND OF THE INVENTION

1. Field of the Invention

Dental devices and especially dental model articulators.

2. Description of the Prior Art

The prior art includes numerous devices for supporting upper and lower dental models for articulation thereon so that adjustments may be made in the reconstruction work being done. Most of these devices employ some sort of support structure or mounting devices for the model from which the models must be removed and repositioned. All dental articulators are similar in many respects and it is important to keep the articulator in centric at all times. The problem with many prior art devices is that there may be unwanted and/or unnoticed movement in the process of working with the articulator. There are various arrangements for holding the upper and lower models and making the necessary adjustments but the present device is simpler, has fewer parts and is easier to make than many prior art devices but at the same time the present device has a versatility which is not found in prior devices, especially with respect to removal and/or adjustment of the mounting bars for the model.

SUMMARY OF THE INVENTION

The present articulator provides horizontal movement on the lower part and for the lower model and vertical movement on the upper part for the upper model, with mounting bars for the models which are not to be reused.

One object of the present invention is to provide disposable mounting bars not to be reused and which are left in the plaster that holds the upper model in place to be sent to the dentist so that the mounting fit between the upper and lower models can be checked. According to the present device, it is unnecessary to mail or send the articulators with the models since the mounting bars remain as a permanent part of the models and may be inserted in another articulator of the same type.

Another object of the present invention is to provide a device and arrangement for the mounting of the upper and lower models which gives a better anterior function and provides a better overall restoration. It is unnecessary for remakes on the same model to go through the plaster department.

An advantage of the present invention is that the dentist is able to see exactly how the case was mounted with the particular bite involved and also permits the dentist to file the models for easy remounting and future reference.

The present device also has the advantage of permitting more "jaw" movement than the conventional articulators.

Another advantage of the present invention is in saving time by eliminating the "knocking off" of models before the delivery thereof.

Other and further objects and advantages of my invention will become apparent upon reading the following specification taken in conjunction with the accompanying drawings.

BRIEF DESCRIPTION OF THE DRAWINGS

FIG. 2 is a bottom plan view of the assembled articulator shown in FIG. 1.

FIG. 3 is a top plan view of the assembled articulator shown in FIGS. 1 and 2.

FIG. 4 is a right side elevation view of the articulator shown in FIG. 1.

FIG. 5 is a left elevation view of the articulator shown in FIG. 1.

FIG. 6 is a front elevation view of the articulator shown in FIGS. 4 and 5.

FIG. 7 is a rear elevation view of the articulator shown in FIGS. 4 and 5.

DESCRIPTION OF A PREFERRED EMBODIMENT

Figure 1:
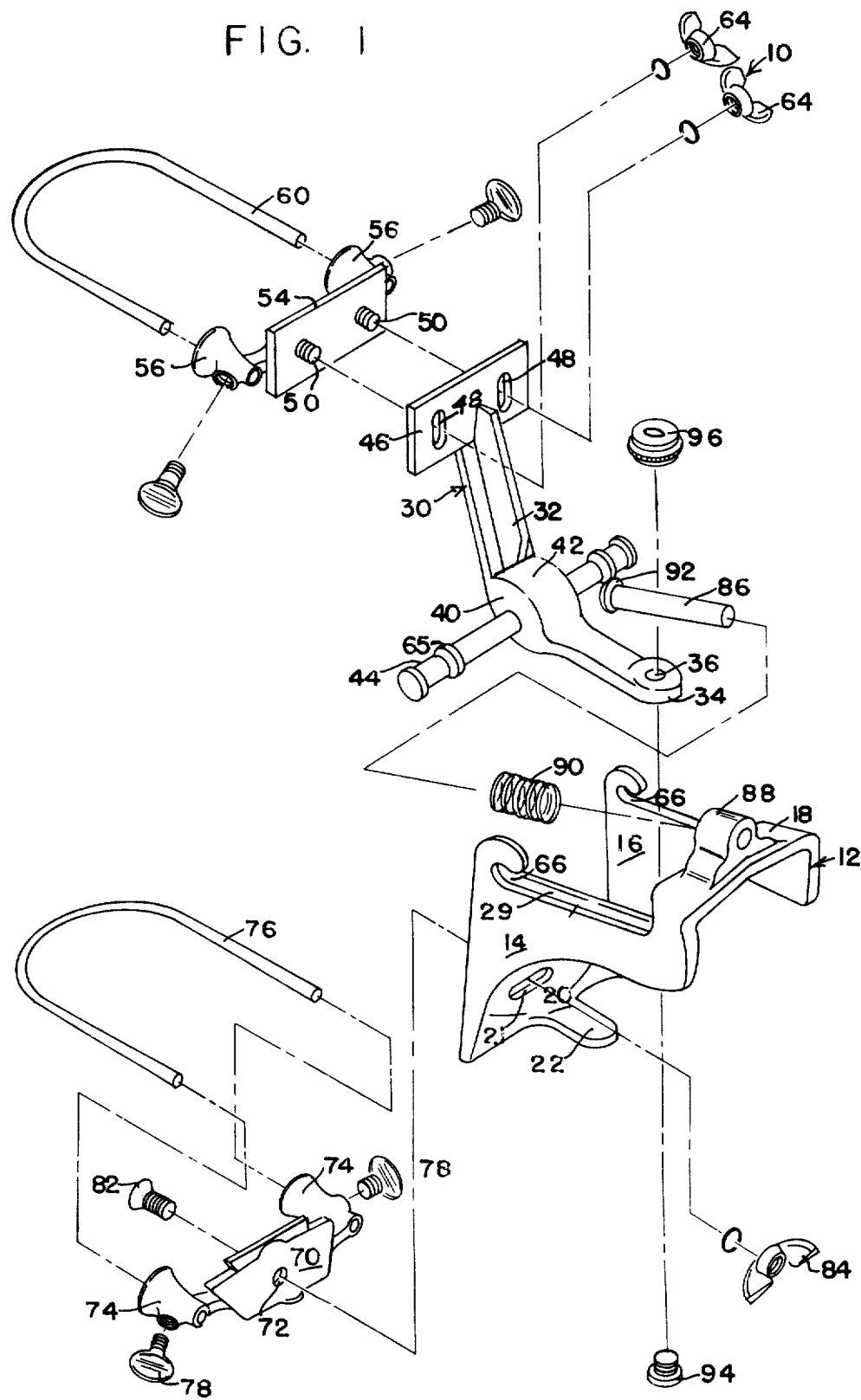
FIG. 1 is a dissembled assembly view of the present articulator.

The complete and assembled articulator which is shown in the drawings herein is designated generally by reference numeral 10 and comprises a base frame designated generally by reference numeral 12 which is manufactured from cast metal or other material to provide a base employing side plates 14, 16, a top transverse connecting base plate 18 normally lying in substantially horizontal position, and a front, usually substantially vertical support plate 20 having a foot 22 projecting therefrom to support the base 12 stably on a flat surface such as a table or desk. Plate 20 has an elongated, horizontal slot 21 therein. Side plates 14, 16 have respective top, open slots 24, 26 defined by inwardly turned members 28. The top edge of side 14 has a groove 29.

An upper pivoting frame designated generally by reference numeral 30 comprises an upper arm member 32 and a lower arm member 34 on which there is an elongated circular portion 35 having a screw opening 36. Arm 32 is reinforced by a rib member 38. A center portion 40 between arms 32 and 34 has a bearing surface 42 thereon from which extends a transverse mounting pin 44. The upper arm member 32 has a transverse upper plate 46 made integral therewith and in which there are a pair of vertical adjusting slots 48 which receive a pair of respective upper adjusting studs 50 mounted on an upper adjusting plate 54 having spaced trumpet-shaped mounting sleeves 56 attached thereto with enlarged bores receiving the ends of a removable mounting bar 60 of generally U-shaped configuration which has the ends inserted into a bore in respective sleeve 56 and held in place therein by means of a respective set screw 62. The holes 48 in plate 46 cooperate with the studs 50 which are adjustably tightened by butterfly nuts 64 to provide the vertical adjustment of the articulation of the upper and lower model through the vertical movement of only the top or upper model which is permanently mounted by plaster on the removable bar 60. Mounting pin 44 has a circular projection 65 on one end to ride in groove 29, and pin 44 fits into spaced notches 66.

The lower model is removably mounted on a lower bracket designated generally by reference numeral 68 and comprising an elongated flat, lower mounting plate 70 having a mounting screw hole 72 extending horizontally therein and having attached thereto a pair of trumpet-shaped, spaced lower mounting sleeves or collars 74 which receive the respective ends of the lower U-shaped mounting bar 76 that are held therein by means of respective set screws 78 in each of the respective mounting collars 74.

The bracket 68 is attached in place on plate 20 on the base 12 by means of a screw 82 fitted through the hole 72 in plate 70 and slot 21 in plate 20 and held in place by a wing nut 84 whereby the bracket 68 may be shifted horizontally by loosening nut 84.

The center portion 40 of the frame 30 is mounted by means of a mounting pin 86 which is inserted through a bearing sleeve 88 on plate 18 to hold a coil spring 90 in place with the head 92 of the pin 86 bearing on bearing surface 42 thereby forcing the projection 64 into groove 29. Thus, the articulation and movement of the top frame 30 on base 12 is accomplished by moving the entire upper pivoting frame 30 on the mounting pin 44 against spring 90. The angle of inclination and position of the top frame 30 is adjusted and set by means of an adjustment screw 94 which is inserted thru the screw opening 36 and lower arm 34 and held in place by a cap nut 96 so that the end of screw 94 bears against the underside of connecting plate 18 of base 12 to determine the fixed position of frame 30 and at the same time limit the movement of the frame 30 in the closing or downward direction toward the lower mounting bar 76. Thus, once set the upper mounting bar 60 will open against spring 90 but cannot close beyond the setting of screw 94, thereby setting the angle of upper mounting bar 60 and of course the model set in plaster therein.

While I have shown and described a particular embodiment of this invention together with a suggested mode of operation this is by way of illustration only since there are various alterations, changes, deviations, departures, omissions and additions which may be made in the embodiment shown without departing from the scope of this invention which is defined only by a proper interpretation of the appended Claims.

What is claimed is:

1. In a dental articulator for mounting a dental model comprising upper teeth and lower teeth:
    a base frame having means thereon for supporting the base stably on a flat surface such as a table or desk,
    a pivoting frame on said base comprising an upper arm extending on said pivoting frame and having a transverse attaching plate formed integrally therewith, said plate having a pair of vertical adjusting slots therein,
    an upper plate having spaced mounting sleeves attached thereto,
    a removable upper model frame having respective terminal ends insertible into a respective sleeve,
    a pressure means for holding said removable upper model frame in place,
    attaching means on said plate to provide the vertical adjustment for the articulation of the upper and lower model thru the vertical movement of only the top,
    a lower bracket comprising a lower model frame and a lower plate,
    a pair of spaced mounting sleeves on said lower plate,
    said lower model frame having respective terminal ends insertible in the respective openings in the mounting sleeves and adjustable pressure means for holding said lower model frame in place.

2. The device in claim 1 including:
    a longitudinal groove formed on said base,
    a mounting pin having a projecting member on said pin extending into said groove and guiding the movement of said pin.

3. The device in claim 2:
    each of said model frames being insertible in a respective opening in a respective sleeve and said opening in said respective sleeve being a completely thru opening and the ends of said respective frame members being insertible therethrough to adjust the position of said respective frame and the respective upper model thereon with respect to the lower model and the base.

4. In a dental articulator device for holding an upper model and a lower model representing the upper teeth and lower teeth:
    a base,
    a movable upper frame on said base for supporting the upper model,
    a pair of spaced frame retaining portions on said movable upper frame and each having an opening extending therethrough,
    an upper model frame support having terminal end portions respectively removably inserted in said openings whereby said model frame support may be permanently attached to the upper model such as by plaster,
    pressure means for removably locking said terminal ends of said upper model frame on said base whereby said upper model frame may be adjusted.

5. The device in claim 4 wherein there is an upper mounting plate on said base and said upper model frame support end portions are movably mounted on said base by means of said upper mounting plate, an elongated substantially horizontal slot on said base, and pressure means extending between said base and said upper model frame.

6. The device claimed in claim 4 wherein said upper model frame support comprises U-shaped frame having the terminal ends thereon, a mounting plate mounted for selective vertical adjustment on said base, and said upper model support frame being attached to said mounting plate.

7. The device in claim 6 wherein said mounting plate has a pair of opposed, elongated vertical slots, and bolts extending thru said slots for adjusting said upper U-shaped frame thereon.

8. The device in claim 4 wherein: there is a lower model support frame on said base, and means for adjusting the lower model support frame horizontally with respect to said base whereby said lower model may be adjusted horizontally with respect to said upper model.

9. The device in claim 8 wherein said means for adjusting the lower model comprises an elongated transverse slot in the base, a lower mounting plate adjustably carried by said base in said slot, and pressure means between said base and lower mounting plate.

10. The device in claim 9 wherein said lower model support frame comprises a U-shaped member having terminal ends, and spaced openings on said lower mounting plate receiving said terminal ends therein.

11. In a dental articulator device for holding an upper model and a lower model representing upper teeth and the lower teeth: a base, a pivoting frame mounted on said base for supporting the upper model thereon, an upper mounting support for said upper model, means for removably mounting said upper mounting support on said pivoting frame whereby the upper mounting support may be removed and repositioned on the same or another identical articulator device, means for vertically adjusting said upper mounting support with respect to said base whereby said upper model may be vertically adjusted, means for adjusting and setting the angle of said pivoting frame on said base, a lower mounting support on said base for said lower model, means for removably mounting said lower mounting support on said base whereby said lower model may be removed and repositioned on the same or another identical articulator device, and means for horizontally adjusting said lower mounting support with respect to said base.

12. The device in claim 11 wherein said pivoting frame has a pivot means thereon, said pivot means being mounted on said base.

13. The device in claim 11 wherein said pivoting frame comprises an upper arm member and a lower member engageable with said base, and spring means interposed between said pivoting frame and said base.

14. The device in claim 13 wherein said pivot means has a guide member thereon and said base has a slot therein in which said guide member travels to align said pivoting frame on said base.

15. The device in claim 11 wherein said upper and lower mounting supports comprise enlarged openings and an upper and lower mounting frame positionable in said openings.

16. The device in claim 11 wherein said means for vertically adjusting comprises a pair of vertical slots on said pivoting frame, and adjustable pressure means such as a bolt for positioning said upper mounting support thereon.

17. The device in claim 8 wherein said means for horizontally adjusting comprises a horizontal slot and adjustable pressure means such as a bolt for positioning said lower mounting support thereon.

18. In a dental articulator device for holding an upper model and a lower model representing upper teeth and the lower teeth: a base, a pivoting frame mounted on said base and said pivoting frame comprising an upper arm and a lower arm, said lower arm being engageable with said base, a pivot pin on said pivoting frame extending from opposite sides thereof, said pivot pin being mounted on said base extending transversely thereacross, a guide member on said pivot pin, a groove on said base in which said guide member is mounted to align said pivoting frame on said base, a mounting pin on said base engageable with said pivoting frame, spring means interposed between said mounting pin and said pivoting frame, an upper portion on said pivoting frame, a pair of vertical slots in said upper portion, a mounting plate having a pair of spaced openings therein, an upper mounting support for said upper model having terminal ends inserted in said spaced openings, a lower mounting plate, a horizontal slot in said base, adjustment means such as a bolt for mounting said lower mounting plate in said slot, a pair of spaced openings in said lower mounting plate, a lower mounting support for said lower model having terminal ends inserted in the spaced openings, and pressure means such as a bolt for adjustably mounting said lower mounting plate in said slot.

19. The device in claim 18 wherein said spaced openings are enlarged so that a respective upper or lower mounted support may be shifted in the openings.

* * * * *